United States Patent [19]

Mueller-Lehar

[11] Patent Number: 5,247,091
[45] Date of Patent: Sep. 21, 1993

[54] PREPARATION OF ENAMINES IN AQUEOUS MEDIA

[75] Inventor: Juergen Mueller-Lehar, Warwick, R.I.

[73] Assignee: Hoechst Celanese Corporation, Somerville, N.J.

[21] Appl. No.: 921,791

[22] Filed: Jul. 30, 1992

[51] Int. Cl.$^5$ .................. C07C 209/22; C07D 219/10
[52] U.S. Cl. .................................... 546/105; 546/79; 546/93; 558/414; 558/418; 560/21; 560/46; 560/47; 560/48; 562/435; 562/453; 562/456; 562/457
[58] Field of Search ............... 558/414, 418; 560/21, 560/46, 47, 48; 562/435, 453, 456, 457; 546/105, 79, 93

[56] References Cited

U.S. PATENT DOCUMENTS 4,631,286 12/1986 Shutske et al. ................. 514/297

OTHER PUBLICATIONS

L. W. Haynes and A. G. Cook in "Enamines—Synthesis, Structure, and Reactions,", 2nd Edition, A. G. Cook, Editor, Marcel Dekker, Inc., New York, N.Y., published 1988, pp. 103 to 114, and Chapter 9.
S. F. Dyke, "The Chemistry of Enamines", Cambridge University Press, London, England, published 1973, pp. 8 and 9.
W. K. Summers, et al., The New England Journal of Medicine, vol. 315, pp. 1241-1245, published Nov. 13, 1986, entitled "Oral Tetrahydroaminoacridine in Long-Term Treatment of Senile Dementia, Alzheimer Type".
A. Osbirk and E. B. Pedersen, Acta Chemica Scandinavica B, vol. 33, published 1979, pp. 313-318, entitled "Phosphoramides, X.* Phosphorous Pentaoxide Amine Mixtures and HMPT as Reagents in the Synthesis of 4-Amino- and 4-Dimethylamino-2,3-polymethylenequinolines".
Acridines, edited by R. M. Acheson, Second Edition, John Wiley & Sons, Inc., published 1973, p. 476.
W. P. Brian and B. L. Souther, Journal of Medicinal Chemistry, vol. 8, pp. 143 to 144, published Jan., 1965, entitled "New Derivatives of 9-Amino-1,2,3,4-tetrahydroacridine".
G. K. Patnaik, et al., Journal of Medicinal Chemistry, vol. 9, pp. 483 to 488, published Jul., 1966, entitled "Compounds Acting on the Central Nervous System, IV. 1-Substituted 2,3-Polymethylenequinolines".
E. T. Michalson, et al., Heterocycles, vol. 30, pp. 415-425, published 1990, entitled "Synthesis of 9-(-1-Azetidinyl)-1,2,3,4-tetrahydroacridine".
U. Edlund, Acta. Chemica Scandinavica, vol. 26, p. 2972, published 1972, entitled "2-(N-Pyrrolidyl)indene; an Enamine of Unusual Stability".
P. K. Khandelwal and B. C. Joshi, Defense Science Journal, vol. 21, pp. 199 and 200, published 1971, entitled "Preparation of 2-(N-Morpholinyl)indene and Its Unusual Stability".
P. W. Hickmott, Tetrahedron, vol. 38, pp. 2005 to 2007, published 1962, entitled "Enamines: Recent Advances in Synthetic, Spectroscopic, Mechanistic, and Stereochemical Aspects-I".

Primary Examiner—Richard L. Raymond
Attorney, Agent, or Firm—Raymond R. Wittekind

[57] ABSTRACT

The synthesis of enamines in aqueous media and a process for the preparation of memory enhancing 9-amino-1,2,3,4-tetrahydracridines are described.

46 Claims, No Drawings

PREPARATION OF ENAMINES IN AQUEOUS MEDIA

Enamines are generally prepared in non-aqueous media with removal of the formed water by azeotropic distillation with an aromatic solvent such as benzene, by the use of drying agents such as molecular sieves, and by the use of water scavengers such as titanium tetrachloride. While these methods provide enamines in good yields and of sufficient purity for subsequent conversions to products of commercial significance, the use and disposal of aromatic solvents, molecular sieves, and titanium halides present a health hazard and degrade the environment, and diminish the cost effectiveness of processes for the preparation of such compounds as intermediates for the synthesis of medicinal or other products of commerce. See, for example, L. W. Haynes and A. G. Cook in "Enamines—Synthesis, Structure, and Reactions," 2nd Edition, A. G. Cook, Editor, Marcel Dekker, Inc., New York, N.Y., 1988, pages 103 to 114, and Chapter 9.

Applicant has now found that the enamines of cycloalkanones and cycloalkandiones and anilines can be prepared in high yield and high purity in aqueous media under conditions commonly used to cleave enamines, thereby avoiding the health and environmental hazards associated with the water removal and drying methods, used previously, and improving the cost effectiveness of commercial processes employing enamines. See, for example, S. F. Dyke, "The Chemistry of Enamines," Cambridge University Press, London, England, 1973, pages 8 and 9.

The present invention relates to a process for the synthesis of enamines of cycloalkanones and cycloalkandiones and anilines in aqueous medium. More particularly, the present invention relates to a process for the synthesis of enamines of formula 1

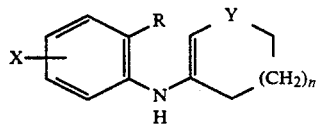

wherein R is CN, CO$_2$H, or CO$_2$R$^1$ wherein R$^1$ is loweralkyl; Y is CH$_2$ or C=O; X is hydrogen, loweralkyl, loweralkoxy, halogen, hydroxy, nitro, NHCOR$^2$ wherein R$^2$ is loweralkyl, or a group of the formula NR$^3$R$^4$ wherein R$^3$ and R$^4$ are independently hydrogen or loweralkyl; and n is 0, 1, or 2, which comprises condensing an aniline of formula 2

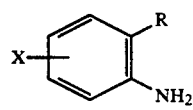

wherein R and X are as hereinbeforedefined with a cycloalkanone or -dione 3

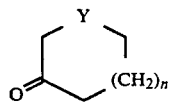

wherein Y and n are as hereinbeforedefined in aqueous medium containing an acidic promoter to provide 1. The condensation is conveniently preformed by mixing the components in an aqueous medium, heating the mixture, if necessary, and after the appropriate reaction time, isolating the enamine 1 by conventional methods, preferably filtration of the reaction mixture.

The preferred aqueous medium is water containing an acidic promoter. Cosolvents such as alkanols, e.g., ethanol, 2-propanol, 1,1-dimethylethanol, and the like, may be employed, however, to facilitate the condensation by dissolution of components 2 and 3. The condensation proceeds at a reasonable rate at temperatures from about −10° C. to about the reflux temperature of the reaction medium, the reaction temperature being dependent on the nature of the components 2 and 3. Lower temperatures are, for example, generally employed when component 3 wherein Y is C=O is used; higher temperatures when component 3 wherein Y is CH$_2$ is used. A condensation temperature of about 40° C. is preferred when a dione 3 wherein Y is C=O is used; a condensation temperature about the reflux temperature of the medium is preferred when an one 3 wherein Y is CH$_2$ is used.

The condensation reaction of aniline 2 and cycloalkanone or -dione 3 is usually complete within about one hour when component 3 wherein Y is C=O is used; about 3 days when component 3 wherein Y is CH$_2$ is used. Longer reaction times are generally, however, not detrimental.

For purposes of economy, equimolar amounts of aniline 2 and cycloalkanone or -dione 3 are usually employed in the condensation reaction. An excess (ca 10%) of aniline 2 may be used to further facilitate the reaction.

Under the hereinbeforementioned conditions, the condensation of an aniline 2 and a cycloalkanone or -dione 3 proceeds at a convenient rate to provide the desired enamine 1 in good yield and a high state of purity. To facilitate the condensation, an acid promoter such as a mineral acid or an organic acid is used. Among mineral acids, there may be mentioned hydrohalic acids such as hydrochloric acid, hydrobromic acid, and hydriodic acid, nitric acid, sulfuric acid, and phosphoric acid. Among organic acids, there may be mentioned carboxylic acids such as acetic acid and trifluoroacetic acid, and sulfonic acids such as benzenesulfonic acid, 4-methylbenzenesulfonic acid, methanesulfonic acid, and ethanesulfonic acid. Hydrochloric acid is the preferred mineral acid; 4-methylbenzenesulfonic acid is the preferred organic acid.

The intermediate enamines 1 provided by condensation of an aniline 2 with a cycloalkanone or -dione 3, the process of the present invention, are useful for the preparation of memory enhancing 9-amino-1,2,3,4-tetrahydroacridines 4

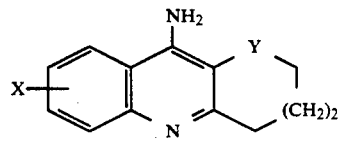

wherein X, Y, and n are as hereinbeforedescribed by conventional cyclization methods. When, for example, 2-cyanoaniline 2 wherein R is CN and X is hydrogen and cyclohexanone 3 wherein Y is CH$_2$ and n is 1 are condensed, 2-(cyclohexen-1-yl)aminobenzonitrile 1 wherein R, X, Y, and n are as above is obtained, which is cyclized to 9-amino-1,2,3,4-tetrahydroacridine by means of a metal halide, the metal being selected from the transition elements of the Periodic Chart of Elements (e.g. scandium, titanium, vanadium, chromium, iron, cobalt, nickel, copper, and zinc) and lithium and the halide from chloride, bromide, or iodide. Cuprous chloride is generally employed as the condensation catalyst. See, for example, U.S. Pat. No. 4,631,286 issued Dec. 23, 1986 to G. M. Shutske and F. A. Pierrat for the cyclization of related enamines and W. K. Summers, et al., New England Journal of Medicine, 315, 1241 (1986) for a discussion of the cognition activating properties of the ultimate product.

When, also for example, 2-cyanoaniline 2 wherein R is CN and X is hydrogen is condensed with 1,3-cyclohexandione 3 wherein Y is C=O, 2-(3-oxocyclohexen-1-yl)aminobenzonitrile 1 wherein R is CN, X is hydrogen, Y is C=O, and n is 1 is obtained, which is cyclized by cuprous chloride to 9-amino-3,4-dihydroacridin-1(2H)-one 4 wherein X is H, Y is C=O, and n is 1 and reduced to 9-amino-1,2,3,4-tetrahydroacidin-1-ol 5

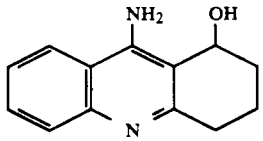

by an alkali metal aluminum hydride (e.g., lithium aluminum hydride) in an ethereal solvent (e.g., diethyl ether, 1,2-dimethoxymethane, 2-methoxyethyl ether, tetrahydrofuran or dioxane) or an alkali metal borohydride (e.g., sodium borohydride) in an aqueous medium (e.g., aqueous 2-propanol) at a reaction temperature of about $-20°$ to about $20°$ C. See U.S. Pat. No. 4,631,286, cited above, for a description of the cyclization of 1 to 4, the reduction of 4 to 5, and the memory enhancing properties of aminoacridine 5.

The reduction of 4 to 5 may also be carried out by catalytic hydrogenation (e.g., by hydrogen in glacial acetic acid, ethanol, or 2-propanol at a hydrogen pressure of about 10 to about 350 psig and a temperature of $20°$ to $80°$ C. in the presence of palladium, platinum, rhodium, or ruthenium, free or supported on, for example, carbon or strontium carbonate).

The condensation of an aniline 2 and cycloalkanone or -dione 3 may be carried out in a one-pot reaction sequence without isolation of the intermediate enamine 1 to provide a 9-amino-1,2,3,4-tetrahydroacridine 4 in good yield and pure state. For example, treatment of 2-aminobenzontirile 2 wherein R is CN and X is hydrogen with cyclohexanone 3 wherein Y is CH₂ and n is 1 in the presence of concentrated hydrochloric acid and cuprous chloride at the reflux temperature of the medium affords pure 9-amino-1,2,3,4-tetrahydroacridine 4 wherein X is hydrogen, Y is CH₂, and n is 1 in high yield.

The ultimate 9-amino-1,2,3,4-tetrahydroacridines 4 are, as hereinbeforementioned, obtained either directly or via the intermediate enamines 1 of the present invention when 2-aminobenzonitriles 2 wherein R is CN are employed as one of the reactants. When, however, 2-aminobenzoic acids 2 (or esters thereof) wherein R is $CO_2H$ or $CO_2R^1$ wherein $R^1$ is loweralkyl are employed, enamines 1 wherein R is $CO_2H$ or $CO_2$loweralkyl are obtained. Enamines 1 wherein R is $CO_2H$ or $CO_2$loweralkyl may be converted to enamines 1 wherein R is CN or cyclized to 9-oxoacridines 6

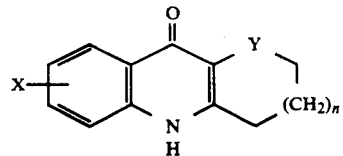

wherein X, Y, and n are as hereinbeforedescribed, which, in turn, may be converted to 9-aminoacridines 4 by methods known in the art. See, for example, A. Oshirk and E. B. Pederson, Acta Chemica Scandinavica B, 33, 313 (1979).

The enamine intermediates of the present invention are recovered by ordinary separation techniques, usually filtration.

The starting materials for the enamine and acridine synthesis of the present invention, i.e., the 2-aminobenzonitriles 2 and 2-aminobenzoic acids 2 (and esters thereof) and cycloalkanones and -diones 3 are commercially available or preparable by conventional methods.

As used through the specification and appended claims, the term "alkyl" refers to a straight or branched chain hydrocarbon radical containing no unsaturation and having 1 to 10 carbon atoms such as methyl, ethyl, 1-propyl, 2-propyl, 1-butyl, 1-pentyl, 2-pentyl, 3-hexyl, 4-heptyl, 2-octyl, 3-nonyl, 4-decyl and the like; the term "alkoxy" refers to a monovalent substituent which consists of an alkyl group linked through an ether oxygen and having its free valence bond from the ether oxygen such as methoxy, ethoxy, propoxy, butoxy, 1,1-dimethylethoxy, pentoxy, 3-methylpentoxy, 2-ethylpentoxy, 2-methyloctoxy, octoxy, decoxy, and the like; the term "halogen" refers to a member of the family fluorine, chlorine, bromine or iodine. The term "lower" as applied to any of the aforementioned groups refers to a group having a carbon skeleton containing up to and including 7 carbon atoms.

The following examples are for illustrative purposes only are not to be construed as limiting the invention. All temperature are given in degree centigrade (°C.).

EXAMPLE 1

A mixture of 2-aminobenzonitrile (120 g) and 1,3-cyclohexandione (120 g) in water (400 ml) was heated to 40° and 4-methylbenzenesulfonic acid monohydrate (6.2 g) was added, with stirring. The mixture was stirred at 40° for 1 hr. The mixture was filtered, and the filter cake was washed with water to provide 200 g (93%) of 2-(3-oxocyclohexen-1-yl)aminobenzonitrile, mp 191.4°.

EXAMPLE 2

A mixture of 2-aminobenzonitrile (120 g), cyclohexanone (115.8 ml), conc hydrochloric acid (9.2 ml), and cuprous chloride (1.21 g) was heated under reflux for 3 days, with stirring. At the end of each 24 hr period, additional cuprous chloride (1.21 g) was added. At the end of the 3rd day, additional conc hydrochloric acid (47.3 ml) was added, and the mixture was cooled to ambient temperature. The precipitate was collected and washed with 10% hydrochloric acid to provide 160 g (67.0%) of 9-amino-1,2,3,4-tetrahydroacridine hydrate, mp 180°–185°.

I claim:

1. A process for the preparation of a compound of the formula

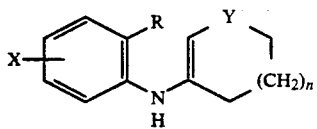

wherein R is CN, CO$_2$H, or CO$_2$R$^1$ wherein R$^1$ is loweralkyl; Y is CH$_2$ or C=O; X is hydrogen, loweralkyl, loweralkoxy, halogen, hydroxy, nitro, NHCOR$^2$ wherein R$^2$ is loweralkyl, or a group of the formula NR$^3$R$^4$ wherein R$^3$ and R$^4$ are independently hydrogen or loweralkyl; and n is 0, 1, or 2, which comprises contacting a compound of the formula

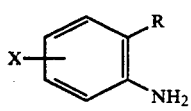

wherein R and X are as above with a compound of the formula

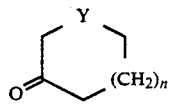

wherein X and n are as above in water in the presence of an acidic promoter.

2. A process according to claim 1 wherein R is CN; Y is CH$_2$; X is hydrogen; and n is 1.

3. A process according to claim 1 wherein R is CN; Y is C=O; X is hydrogen; and n is 1.

4. A process according to claim 1 wherein the a co-solvent is employed.

5. A process according to claim 1 wherein the acidic promoter is an organic acid.

6. The process according to claim 5 wherein the organic acid is 4-methylbenzenesulfonic acid.

7. A process according to claim 1 wherein the acidic promoter is a mineral acid.

8. The process accordingly to claim 7 wherein the mineral acid is hydrochloric acid.

9. The process according to claim 1 wherein the reaction is carried out at a temperature of from about −10° C. to about the reflux temperature of the reaction medium.

10. The process according to claim 9 wherein the reaction is carried out at a temperature of about 40° C.

11. The process according to claim 1 wherein the reaction is carried out at about the reflux temperature of the reaction medium.

12. A process for the preparation of a compound of the formula

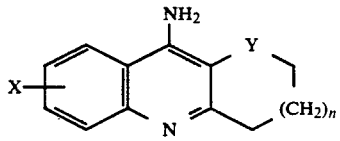

wherein X is hydrogen, loweralkyl, loweralkoxy, halogen, hydroxy, nitro, NHCOR$^2$ wherein R$^2$ is loweralkyl, or a group of the formula NR$^3$R$^4$ wherein R$^3$ and R$^4$ are independently hydrogen or loweralkyl; Y is CH$_2$ or C=O; and n is 0, 1, or 2, which comprises contacting a compound of the formula

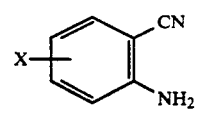

wherein X is as above with a compound of the formula

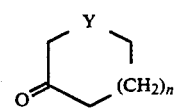

wherein Y and n are as above in water in the presence of an acidic promoter and a cyclization agent.

13. A process according to claim 12 wherein X is hydrogen, Y is CH$_2$, and n is 1.

14. A process according to claim 12 wherein X is hydrogen, Y is C=O, and n is 1.

15. A process according to claim 12 wherein the acidic promoter is an organic acid.

16. The process according to claim 15 wherein the organic acid is 4-methylbenzenesulfonic acid.

17. A process according to claim 11 wherein the acidic promoter is a mineral acid.

18. The process according to claim 17 wherein the mineral acid is hydrochloric acid.

19. A process according to claim 12 wherein the cyclization agent is a halide of a metal selected from the group consisting of the transition elements of the Periodic Chart of Elements and lithium.

20. A process according to claim 19 wherein the halide is selected from the group consisting of bromide, chloride, or iodide.

21. The process according to claim 20 wherein the halide is chloride.

22. The process according to claim 19 wherein the transition metal is copper.

23. The process according to claim 22 wherein the transition metal is copper$^{+1}$.

24. The process according to claim 23 wherein the cyclization agent is cuprous chloride.

25. The process according to claim 12 wherein the reaction is carried out at the reflux temperature of the reaction medium.

26. A process for the preparation of a compound of the formula

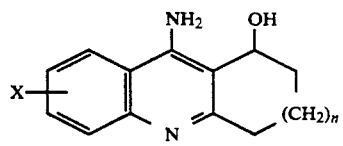

wherein X is hydrogen, loweralkyl, loweralkoxy, halogen, hydroxy, nitro, NHCOR$^2$ wherein R$^2$ is loweralkyl, or a group of the formula NR$^3$R$^4$ wherein R$^3$ and R$^4$ are independently hydrogen or loweralkyl; and n is 0, 1, or 2, comprising the steps of (a) contacting a compound of the formula

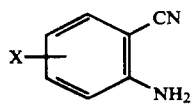

wherein X is as above with a compound of the formula

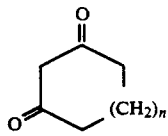

wherein n is as above in water in the presence of an acidic promoter to provide a compound of the formula

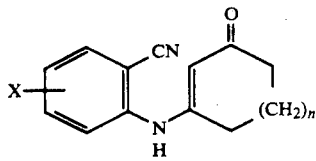

wherein X and n are as above; (b) cyclizing the compound obtained in step (a) to a compound of the formula

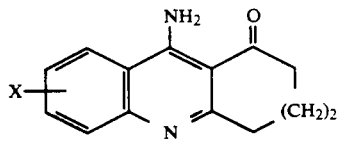

wherein X and n are as above; (c) reducing the compound obtained in step (b); and (c) isolating the product.

27. A process according to claim 26 wherein the acidic promoter of step (a) is a mineral acid.

28. The process according to claim 27 wherein the mineral acid is hydrochloric acid.

29. A process according to claim 27 wherein the acidic promoter is an organic acid.

30. The process of claim 29 wherein the organic acid is 4-methylbenzenesulfonic acid.

31. The process according to claim 26 wherein the reaction of step (a) is carried out at a temperature of from about $-10°$ C. to about the reflux temperature of the reaction medium.

32. The process according to claim 28 wherein the reaction of step (a) is carried out at about 40° C.

33. A process according to claim 26 wherein the cyclizing agent employed in step (b) is a halide of a metal selected from the group consisting of the transition elements of the Periodic Chart of Elements and lithium.

34. The process according to claim 33 wherein the transition metal is copper.

35. The process according to claim 34 wherein the cyclizing agent is copper$^{+1}$ chloride.

36. A process according to claim 26 wherein the reducing agent in step (c) is alkali metal aluminum hydride.

37. The process according to claim 36 wherein the alkali metal aluminum hydride is lithium aluminum hydride.

38. A process according to claim 26 wherein the reducing agent of step (c) is alkali metal borohydride.

39. The process according to claim 38 wherein the alkali metal borohydride is sodium borohydride.

40. A process according to claim 26 wherein a solvent is employed.

41. A process according to claim 40 wherein the solvent is an ethereal solvent when an alkali metal aluminum hydride is employed in step (c).

42. A process according to claim 41 wherein the ethereal solvent is selected from the group consisting of diethyl ether, 1,2-dimethoxyethane, 2-methoxyethylether, tetrahydrofuran, and dioxane.

43. A process according to claim 26 wherein the reduction of step (c) is carried out at a temperature within the range of about $-20°$ to about 20° C.

44. The process according to claim 43 wherein the solvent is an aqueous alkanol when an alkali metal borohydride is employed.

45. The process of claim 44 wherein the aqueous alkanol is aqueous 2-propanol.

46. A process according to claim 26 wherein the steps (a) and (b) are carried out in a one-pot reaction without isolating the product of step (a).

* * * * *